United States Patent
Derreumaux

(10) Patent No.: US 6,864,797 B2
(45) Date of Patent: Mar. 8, 2005

(54) METHOD AND DEVICE FOR CARRYING OUT THE PROTECTED DETECTION OF THE POLLUTION OF WATER

(75) Inventor: Luc Derreumaux, Neuilly sur Seine (FR)

(73) Assignee: Compagnie Industrielle de Filtration et d'Equipement Chimique (CIFEC), Neuilly sur Seine (FR)

(*) Notice: Subject to any disclaimer, the term of this patent is extended or adjusted under 35 U.S.C. 154(b) by 107 days.

(21) Appl. No.: 10/442,827

(22) Filed: May 21, 2003

(65) Prior Publication Data

US 2003/0217590 A1 Nov. 27, 2003

(30) Foreign Application Priority Data

May 23, 2002 (FR) ............................................. 02 06313

(51) Int. Cl.[7] ............................................. G08B 21/00
(52) U.S. Cl. ..................... 340/621; 340/603; 119/215
(58) Field of Search ................................ 340/603, 605, 340/607, 608, 618, 619, 621, 622; 119/215, 219, 268; 43/17.1, 17.5; 702/2

(56) References Cited

U.S. PATENT DOCUMENTS

| 3,805,224 A | 4/1974 | Wenz ........................... 367/93 |
| 4,626,992 A | 12/1986 | Greaves et al. ............. 600/300 |
| 4,805,337 A | * 2/1989 | Kurata ........................ 43/17.5 |
| 5,903,305 A | * 5/1999 | Yamamoto .................... 348/61 |
| 6,058,763 A | * 5/2000 | Shedd et al. ............... 73/61.41 |

FOREIGN PATENT DOCUMENTS

| FR | 2 573 875 | 5/1986 |
| FR | 2 769 713 | 4/1999 |
| FR | 2 769 714 | 4/1999 |
| JP | 2003139764 A | * 5/2003 |

* cited by examiner

Primary Examiner—Van T. Trieu
(74) Attorney, Agent, or Firm—William A. Drucker

(57) ABSTRACT

The method according to the invention consists in providing two containers fed by the water source whose pollution is desired to be measured, each of the containers containing fish and being equipped with a detector able detect any abnormal behaviour of the fish, alternate the lighting and obscurity periods for said two containers, carry out the detection of the behaviour of the fish in the two containers and trigger an alarm signal when the detection shows an abnormal behaviour of the fish.

17 Claims, 1 Drawing Sheet

METHOD AND DEVICE FOR CARRYING OUT THE PROTECTED DETECTION OF THE POLLUTION OF WATER

BACKGROUND OF THE INVENTION

1. Field of the Invention

The present invention concerns a method and device allowing the protected detection of the pollution of water.

2. Description of the Prior Art

Generally speaking, it is known that so as to detect pollution thresholds, the fish, usually trout, are placed in a container inside which the water is to be controlled circulates, and parameters representing the behaviour of the fish are detected. An alarm signal is transmitted when the detected parameters show an abnormal behaviour of the fish, said alarm likely to be generated by a pollution threshold being exceeded.

Thus, in particular in the French patent No. 98 01387 filed in the name of the applicant, a method is being proposed consisting of:

generating in the water of the container a series of ultrasonic wave trains spaced from one another by periods of silence, detecting during the periods of silence the echoes generated by each of said trains, carrying out the temporal analysis of said echoes and memorising the results of theses analyses, comparing the results of the time analyses of the echoes resulting from each wave train with reference values and/or with the results of the time analysis of the echoes resulting from the preceding wave train, determining the degree of pollution of the water according to the results of said comparison.

This method is based on the fact that the form and the layout of the echoes (variation in the process of time of analysis of the signal) depend on the position of the various obstacles and that consequently, by comparing the form of various echoes detected during two successive silent periods, it is possible to determine a modification of the movement of the fish. In the case of no movement occurring, the echoes shall always be identical and there shall be no difference between two successive echoes. On the other hand, when the fish move, the difference between two echoes is proportional to the amount of movement. An alarm could be triggered below or above an adjustable threshold between two echoes.

This solution proves to have a significant drawback owing to the fact that like most animals, trout are subject to going to sleep. Consequently, during periods of sleep, usually at night, the behaviour of the trout is closely related to abnormal behaviour giving rise to the transmission of the alarm signal. As a result, false signals are triggered, thus rendering this method unusable during the periods when the trout are likely to sleep.

OBJECT OF THE INVENTION

Thus, the aim of the invention is more specifically to eliminate these drawbacks.

To this effect, this aim is based on the fact that it is possible to artificially provoke periods of sleep for the fish by placing the containers under artificial lighting and by alternating lighting periods and periods of obscurity.

SUMMARY OF THE INVENTION

Consequently, the method according to the invention consists of:

providing two containers fed by the water source whose pollution is desired to be measured, each of said two containers containing fish and being equipped with means able to detect an abnormal behaviour of said fish, Alternating lighting and obscurity periods of the two containers so that when one of the two containers is lit up, the other one is in obscurity or vice versa, Carrying out detection of the behaviour of the fish in the two containers, and Triggering an alarm signal when said detection shows an abnormal behaviour of the fish depending on whether the container is lit up or not.

By means of this arrangement, it is possible to continuously carry out the detection of the pollution without said detection being disturbed by the sleep periods of the fish which exclusively occur during the periods when the containers are in obscurity.

Of course, the information resulting from the detection carried out during the periods of obscurity of the containers could be used to validate the behaviour anomalies picked up during the lighting phases. This process could particularly concern a transitory period including the changing of the containers from a lit up period to a period of obscurity. Indeed, the behaviour of the fish during these changes discloses the health of the fish.

BRIEF DESCRIPTION OF THE DRAWINGS

One embodiment of the invention shall be described hereafter by way of non-restrictive example with reference to the accompanying drawings on which.

DESCRITPTION OF THE PREFFERED EMBODIMENTS

In this example, the installation consists of two containers $B_1$–$B_2$ partially filled with water and fed by a common water source for which it is desired to monitor the level of pollution.

These two containers $B_1$–$B_2$ are placed in two cells $C_1$–$C_2$ sealed from the light and each having means $E_1$–$E_2$ able to be controlled by means of a processor 22 so as to provoke an alternation of periods of light and obscurity, the period of lighting of one of the containers $B_1$ corresponding to the obscurity period of the other container $B_2$ and conversely. The lighting periods can overlap so as to take account of awakening and sleep period of the fish. By means of this arrangement, it can be ensured that the fish in one of the two containers are awake whilst the fish in the other container are asleep, are waking up and even going to sleep.

Figure 1:
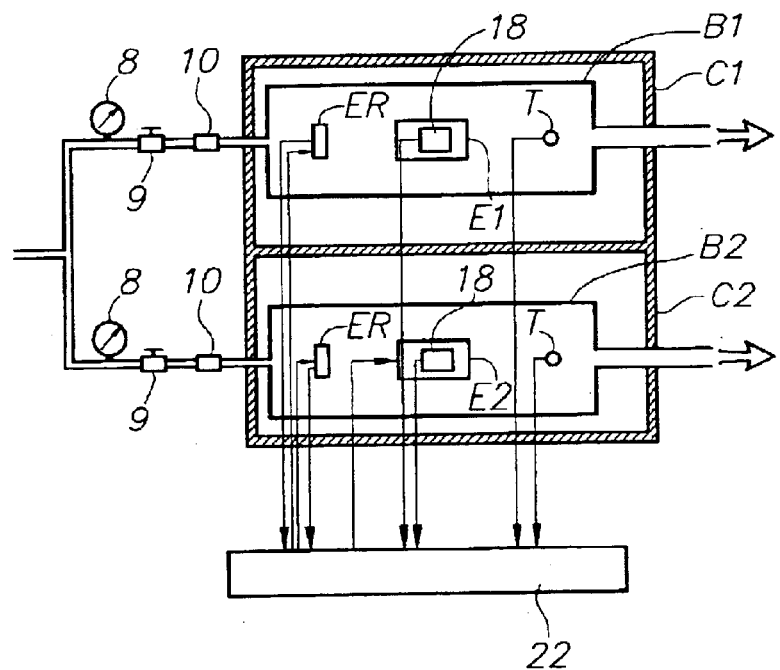
FIG. 1 is a horizontal cutaway diagrammatic representation of the installation according to the invention including two containers.
Figure 2:
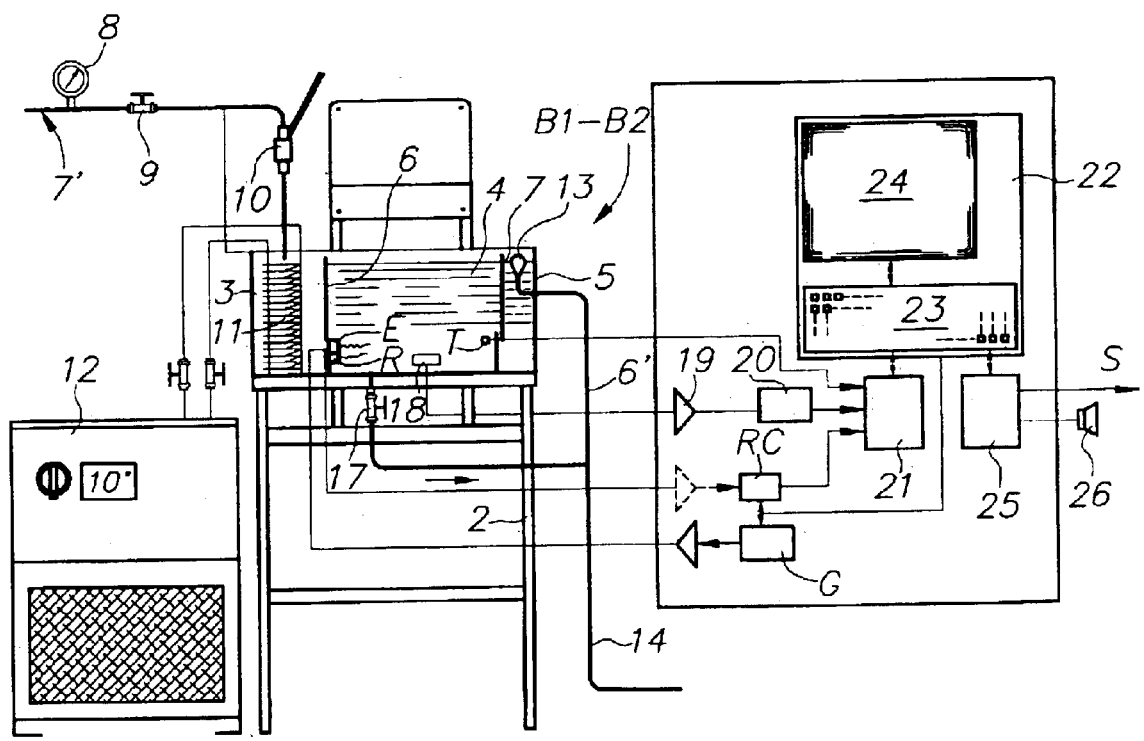
FIG. 2 is a vertical cutaway diagrammatic representation of one of the two containers of the installation shown on FIG. 1.

Each of said containers $B_1$–$B_2$ can be equipped as shown on FIG. 2 and be divided into three chambers 3, 4, 5 by two vertical partitions 6, 7, namely:

a water intake chamber and possibly cooling chamber 3, a main chamber 4 in which the fish are placed, an evacuation chamber 5 provided with an excess circuit 6'.

The intake chamber 3 and the evacuation chamber can be common for the containers $B_1$–$B_2$ with the main chamber 4.

Feeding of each of the containers $B_1$–$B_2$ is carried by a water intake circuit 7' opening into the intake chamber 3 and successively comprising a manometer 8, an adjusting valve 9 and a venture 10 intended to ensure oxygenation of the water.

The intake chamber 3 can contain a heat exchanger 11 (pipe coil) connected to an air-conditioning device 12 adjusted so that the water penetrating into the main chamber 4 via orifices or chicanes, preferably situated in the lower portion of the partition 6, is at a constant temperature (for example less than 15° C.) corresponding to the temperature the fish are accustomed to live. This air-conditioning device 12 can include an automatic control circuit comprising a temperature sensor placed at the outlet of the intake chamber.

The evacuation chamber 5 communicates with the main chamber 4 by means of orifices provided in the partition 7, the overflow circuit 6' whose outlet is fitted with a strainer 13 determining the level of water contained in the container $B_1$. This overflow circuit 6' is connected to a draining circuit 14 which opens into the bottom of the main chamber 4 by means of a drain valve 17.

The water passage orifices made in the partitions 6 and 7 are designed so as to stop fish passing through and ensure a flowing free from turbulence or any hydrodynamic phenomenon likely to generate noticeable pressure waves in the main chamber 4 and of a kind to disturb those made by the fish.

The main chamber 4 is provided with an ultrasound wave transmitter/receiver unit ER whose transmitting portion E is connected to an ultrasound signal generator controlled by a processor 22 whose keypad 23 and screen 24 are diagrammatically represented. Under the control of the processor 22, said generator transmits in the water a series of ultrasonic waves separated from one anther by silent periods. The transmitter/receiver unit also contains a temperature sensor T making it possible, following processing by the circuit 21, to inform the processor 23 of the temperature of the water.

The receiving portion R of the unit ER is connected to a receiving circuit RC, also controlled by the processor 22, so as to receive the echo signal received by the receiving portion during the silent periods.

Following processing by the receiving circuit RC, the echo signal is transmitted to an analysis circuit 21 connected to the processor 22.

By means of these arrangements, all the seconds (adjustable values) during a period of one millisecond (adjustable value), an ultrasonic wave train, for example at 40 kilohertz (adjustable value), could be transmitted by the transmitting portion E into the water of the container $B_1$–$B_2$, which is lit up. These waves are reflected by all the obstacles they meet, mainly by the fish and glass walls of the aquarium. The reflected waves (echoes) are detected during the silent period by the receiving portion which delivers an echo signal whose form (time variation of the amplitude of the signal) depends on the position (particularly of the receiving portion/obstacle distance). Said signal, once digitised by the analysis circuit, is stored and processed by the processor.

This processing could include a comparison of the echo signal obtained following the transmission of a wave train with the echo signal generated by a wave train previously transmitted so as to determine the physiological state of the fish, it being understood that:

in the case of an absence of movement of the fish, the echoes shall still be identical and the difference between two echo signals shall be nil, in the presence of moving fish, the difference of form of two consecutive echo signals is representative of the movement quantity.

Below or above an adjustable difference threshold between two echoes, the processor could trigger an alarm.

As the movement of the fish is dependent on the temperature of the water, the measurement of the movement quantity shall be weighted by the temperature measurement.

The processor could be programmed so as to carry out a digital analysis such as for example the Fourrier Transform of the echo signals, for examining the agitation frequency of the fish and its amplitude, that is parameters indicative of the state or the stress of the fish.

In this example the central chamber 4 is in addition equipped with at least one piezometric sensor 18 connected to the analysis circuit 21 by means of an amplifier 19 and a filter 20.

Following digitisation by the circuit 21, the signals delivered by the sensor 18, which are representative of both the power and speed of the movements and therefore the alertness of the fish, are analysed by the processor 22 so as to detect any abnormal change in the behaviour of the fish (acceleration, fibrillation, slowing down, prolonged absence of movements). This information could be used to validate or complete the information deduced from the echo signals originating from the receiving portion R.

Of course, the processor 22 can be programmed so as to identify the changes in the behaviour of the fish and compare these with a previously memorised typological classification of changes so as to determine the nature of the pollution which has caused these changes and/or orientate chemical researches to the determined polluting agents.

Advantageously, the processor 22 could transmit an alarm signal S by means of an interface 25 and/or continuously draw up an audio signal which, when applied to a loudspeaker 26 or similar element, generates a sound signal whose frequency is proportional to the general agitation of the fish bench present in the chamber 4.

This process could possibly be carried out in a non-lit container in which the fish are supposed to be asleep. Similarly, the processor could be programmed so as to identify the changes in the behaviour of the fish with a view to determine the occurrence of any pollution.

Likewise, the processor could be programmed so as to analyse the behaviour of the fish during moving from an illuminated state to a non-illuminated state or vice-versa, so as to be able for example to clearly see the fish which died during the period of sleep.

These arrangements make it possible to obtain a reliable functioning free of false alarms.

What is claimed is:

1. Protected detection method of the pollution of water, comprising the following steps:

providing two containers fed by a water source whose pollution is desired to be measured, each of these two containers containing fish and being equipped with detection means for detecting an abnormal behaviour of said fish, alternating the periods of lighting and periods of obscurity of said two containers so that when one of said two containers is in a lit up state, the other container is in a state of obscurity and vice versa, carrying out a detection of behaviour of the fish in said two containers, and triggering an alarm signal when said detection of behaviour shows an abnormal behaviour of the fish in one of said two containers according to the said states.

2. Method according to claim 1, comprising said detection of behaviour of the fish during said periods of obscurity in said containers, this detection being used to validate said behaviour anomalies recorded during said periods of lighting.

3. Method according to claim 1, comprising said detection of behaviour of the fish during transitory periods including the passage from said lit-up state to said state of obscurity of said containers.

4. Method according to claim 1, wherein said periods of lighting of said two containers, overlap so as to take account of periods of the fish when waking up and going to sleep.

5. Method according to claim 1, wherein said detection of behaviour of the fish comprises the steps of:
- generating in the water of the container a series of ultrasonic waves trains separated from one another by silent periods,
- detecting during said periods of silence echoes generated by each of said trains,
- carrying out the time analysis of said echoes and storing the results of these time analysis,
- comparing the results of the time analysis of the echoes resulting from each wave train with reference values and/or the results of the time analysis of the echoes resulting from a preceding wave train,
- determining a degree of pollution of the water according to the results of said comparison.

6. Method according to claim 5, wherein said time analysis is weighted by the temperature.

7. Method according to claim 5, comprising a detection of the variation of the amount of movements of the fish by comparing the forms of the echoes detected during two successive silent periods.

8. Method according to claim 7, wherein said variation is detected by the difference between the echoes detected during the two successive silent periods.

9. Method according to claim 7, wherein an alarm is triggered when the difference between the echoes detected during said two successive silent periods falls below or exceeds an adjustable threshold.

10. Method according to claim 5, said method comprising the examination of the frequency of movements of the fish and its amplitude by digital analysis techniques comprising a Fourrier Transform.

11. Method according to claim 5, wherein it further comprises the steps of detecting an amplitude and/or a frequency of pressure variations generated in the water by the movement of the fish and using information resulting from the detecting step so as to complete and/or to validate information resulting from the detection of said echoes.

12. Device for protected detection of the pollution of water, by effecting the following steps:
- providing two containers fed by a water source whose pollution is desired to be measured, each of these two containers containing fish and being equipped with detection means for detecting an abnormal behaviour of said fish,
- alternating the periods of lighting and periods of obscurity of said two containers so that when one of said two containers is in a lit up state, the other container is in a state of obscurity and vice versa,
- carrying out a detection of the behaviour of the fish in said two containers, and
- triggering an alarm signal when said detection of behaviour shows an abnormal behaviour of the fish in one of said two containers according to the said states,
- said device comprising two containers fed by a water source for which it is desired to the measure the pollution and each container containing fish, two sources of lighting respectively intended to light up said containers according to alternate periods of lighting and periods of obscurity so that when one of said two containers is in obscurity, the other one is in lit up state, means for detecting the behaviour of the fish in each of said two containers, and means making it possible to trigger an alarm signal when said detection means detect an abnormal behaviour of the fish.

13. Device according to claim 12, for each of said containers, said device comprising an ultrasonic wave transmitter/receiver unit whose transmitting portion is connected to an ultrasonic wave generator so as to transmit into the water a series of ultrasonic waves trains separated from one another by periods of silent and whose receiving portion is connected to a receiving circuit able to receive the echo signal received by said receiving portion during the periods of silent, and transmit this signal to an analysis circuit.

14. Device according to claim 13, wherein for each of said containers, it further comprises a temperature sensor for the water of the container whose information is transmitted to said analysis circuit.

15. Device according to claim 14, wherein it further comprises a piezometric sensor connected to said analysis circuit at said same time as the temperature sensor of the water.

16. Device according to claim 13, wherein said analysis circuit is connected to a processor.

17. Device according to claim 16, wherein said processor is programmed so as to carry out the Fourrier Transform of the echo signals.

* * * * *